United States Patent [19]

Renton

[11] Patent Number: 4,767,404
[45] Date of Patent: Aug. 30, 1988

[54] SURGICAL SUCTION DEVICE HAVING A PERFORATED SLEEVE

[75] Inventor: Derric Renton, Louisville, Ky.

[73] Assignee: R & S Associates Co., Louisville, Ky.

[21] Appl. No.: 885,447

[22] Filed: Jul. 14, 1986

[51] Int. Cl.⁴ .......................................... A61M 31/00
[52] U.S. Cl. ..................................... 604/48; 604/268;
 604/902; 433/93
[58] Field of Search ............... 433/91, 93, 96; 604/73,
 604/93, 902, 48, 49–54, 65, 66, 264–269,
 275–277

[56] References Cited

U.S. PATENT DOCUMENTS

| | | | |
|---|---|---|---|
| 737,795 | 4/1903 | Van't Woud | 604/275 |
| 2,220,493 | 11/1940 | Pixler | 604/268 |
| 2,804,075 | 8/1957 | Borden | 604/902 |
| 3,191,600 | 6/1965 | Everett | 604/902 |
| 3,308,825 | 3/1967 | Cruse | 604/902 |
| 3,476,759 | 2/1969 | Smith | 604/264 |
| 3,623,483 | 11/1971 | Dyer, Jr. | 604/902 |
| 3,758,950 | 9/1973 | Krouzian | 433/91 |
| 3,848,604 | 11/1974 | Sackner | 128/350 |
| 3,955,573 | 5/1976 | Hanson et al. | 604/902 |
| 3,963,028 | 6/1976 | Cooley et al. | 604/264 |
| 3,965,901 | 6/1976 | Penny | 128/276 |
| 4,022,218 | 5/1977 | Riddick | 128/350 |
| 4,068,664 | 1/1978 | Sharp et al. | 128/276 |
| 4,400,168 | 8/1983 | Boechel et al. | 604/73 |
| 4,487,600 | 12/1984 | Brownlic et al. | 604/93 |
| 4,490,138 | 12/1984 | Lipsky | 604/268 |
| 4,662,871 | 5/1987 | Rafelson | 604/902 |

FOREIGN PATENT DOCUMENTS 1491755 10/1969 Fed. Rep. of Germany .

Primary Examiner—C. Fred Rosenbaum
Assistant Examiner—J. L. Kruter
Attorney, Agent, or Firm—Banner, Birch, McKie & Beckett

[57] ABSTRACT

A perforate suction tip for removal of surgical debris with reduced clogging and with minimum trauma to tissue is disclosed. Suction ports are arranged on the tip so that suction ports which remain unblocked when surgical debris lodges in other suction ports operate as a vacuum modulator facilitating the removal of the blockage. Further, the likelihood of blocking every suction port, thereby aspirating and damaging tissue, is greatly reduced.

11 Claims, 3 Drawing Sheets

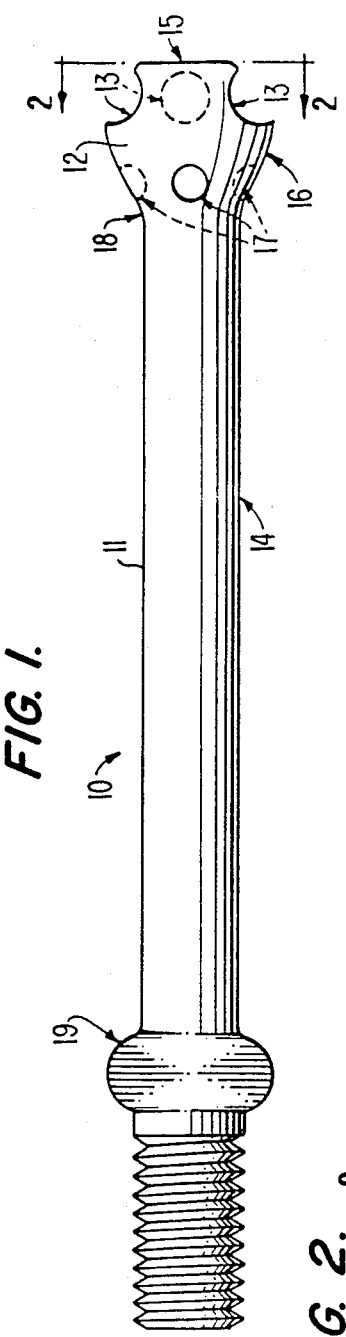
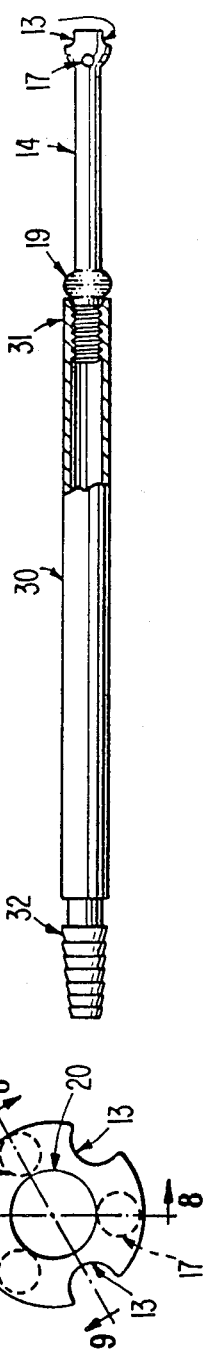
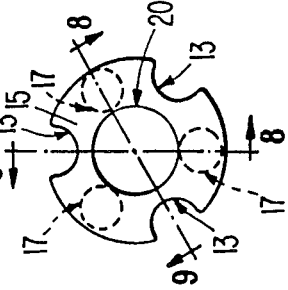
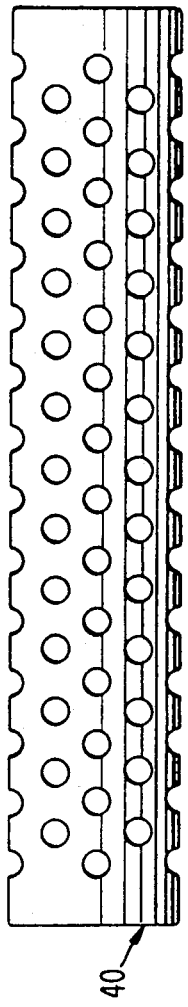
FIG. 1.
FIG. 2.
FIG. 3.
FIG. 4.

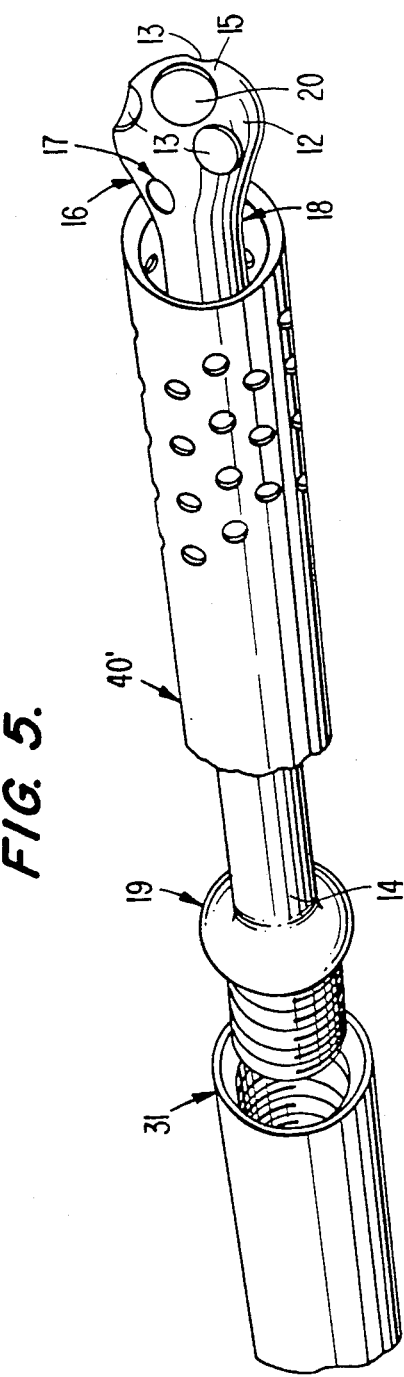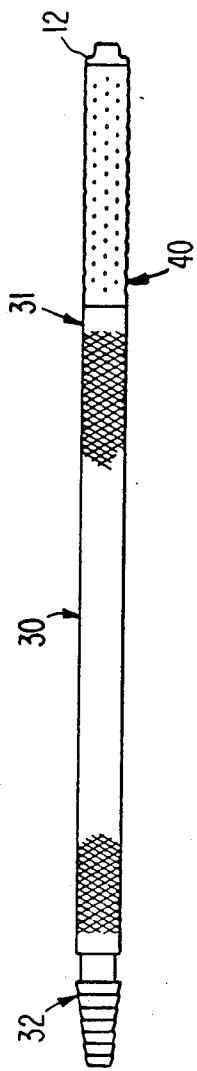
FIG. 5.
FIG. 6.

SURGICAL SUCTION DEVICE HAVING A PERFORATED SLEEVE

BACKGROUND OF THE INVENTION

1. Field of the Invention

This invention relates to surgical suction devices for the removal of surgical debris.

2. Description of the Prior Art

Suction devices are used during surgical procedures to remove fluids and debris from the operating field. Various designs have been proposed for these devices. Typically, such devices include a tip which is inserted into the surgical field and a means, usually a conduit or a tube, for connecting the tip to a vacuum source. However, these known devices have proven unsatisfactory in some aspect.

The designer of a surgical suction device must consider various factors. The device must be easy and convenient to use and must minimize the amount of disruption to the surgeon. The time required to clear the field may impact both the total length of the procedure and the ability of the surgeon to identify problems within the field and complete the procedure. The length of the procedure affects both the surgeon and the patient. Procedures lengthened unnecessarily are unduly tiring to the surgeon and expose the patient to anesthesia for a prolonged period. Therefore, the time required to use the device must be minimized. Ease of use contributes to minimization of the time required to complete the surgery and facilitates operation of the device by less trained personnel.

The device must also minimize the disruption of the patient's tissues. Aspects of disruption which must be considered include the size of the incision required and the trauma to tissue should it be aspirated into the device. The suction device should not require that the operating field be adjusted to accommodate it. Further, it is inevitable that tissue will be exposed to suction through inadvertence or inability to properly clear the field without impinging upon tissue. Therefore, the device should minimize tissue trauma by minimizing both the space required to use it and the tendency to injure aspirated tissue.

Further, the suction device must clear the field effectively. Typically, blood and other fluids, such as saline irrigating fluid and the like, will be present in the operating field. Solids and semi-solids such as coagulated blood, bone chips, excised tissue particles, and the like will also be present. All these materials must be removed from the operating field without extraordinary effort. The device must continue to operate effectively in the presence of these materials without requiring repeated and prolonged interruptions to unblock the device.

Various designs have been proposed to satisfy the above-described factors. For example, devices which control the amount of suction by moving the suction source relative to perforations in the tip are common. See, for example, U.S. Pat. Nos. 3,426,759 and 4,487,600. Some of these devices take advantage of relative motion to attempt to shear blockages of the suction tip, as in U.S. Pat. Nos. 3,308,825 and 4,400,168. However, these designs are, for the most part, not commercially accepted because they are unduly difficult to operate. For example, the design in U.S. Pat. No. 3,308,825 requires that a locknut be loosened to allow the suction tube to slide within the suction tip and adjust the number of holes exposed to suction. The locknut must then be tightened to fix the location of the suction tube in relation to the suction tip. U.S. Pat. No. 4,400,168 requires that the thumb of the user's hand be utilized when varying the number of suction holes exposed and when shearing off blockages. The former procedure is complex while the latter requires a great deal of concentration and manual dexterity. Further, shearing apparatus typically require metal construction, thereby raising costs. Therefore, these designs are less than satisfactory.

Other devices vary the amount of suction available by sliding a suction tube within a perforated tip, as in U.S. Pat. No. 4,487,600, or by providing an opening between the vacuum source and the suction tip, as in German O.S. No. 1,491,755. However, both designs are flawed, the latter being unwieldy to operate, the former tending to clog and make the suction too strong when the suction is directed at only the holes closest to the tip.

Other designs, such as U.S. Pat. No. 3,963,028, while simple to manufacture and operate, are prone to clogging as the tip impinges upon tissue because the holes in the suction tip are relatively closely spaced. Designs which provide for atraumatic withdrawal of blood, such as U.S. Pat. No. 3,623,483, do not provide for adjustment of suction strength. Further, this design requires displacement of tissue within the field and a pool of blood from which to draw. Therefore, it is difficult to use such a design to completely dry a field.

Finally, other designers have circulated anti-coagulant in the tip. The anti-coagulant delivery device described in U.S. Pat. No. 3,955,573 is intended for use in autologous blood transfusion. Therein, anti-coagulant is delivered within a bulbous suction tip designed to thoroughly mix the anti-coagulant with the blood being aspirated. Therefore, the clotting tendency is almost immediately suppressed, thereby preventing clotting and blockages within the device. U.S. Pat. No. 2,804,075 discloses an anti-coagulant delivery system and teaches that when the suction holes become blocked, anti-coagulant accumulates within the tip and usually clears the blocked holes. Further, bone chips are said not be able to block the aspirator because the holes in the suction tip are smaller than the suction tube diameter. However, this does not explain why a bone chip might not block the suction tip itself nor how a blockage which is not affected by anti-coagulant, such as a flat globule or a piece of excised tissue, would be removed.

None of these devices have proven to be satisfactory. Therefore, it is an object of this invention to provide a surgical suction device which is convenient to use, clog resistant, efficient, and able to quickly clear an operating field of surgical debris while minimizing damage to tissue. It is a further object of this invention to provide a surgical suction device wherein the suction ports are disposed in a fashion which ensures that at least some of the suction ports will remain unclogged.

SUMMARY OF THE INVENTION

In accordance with these and other objectives, this invention relates to a suction device to be attached to a vacuum source for removal of surgical debris comprising an elongated section through which the debris is aspirated. The elongated section contains a perforate end section in communication with a hollow central suction conduit which forms a passageway for the aspirated debris. The perforate end section has a perforate first surface portion extending from the end of the elongated section to the widest part of the perforate end section, and a perforate second surface portion extending from the widest part of the perforate end section to the distal end of the end section. Perforations form suction ports for the aspiration of debris through suction port conduits which communicate between the suction ports and the hollow central suction conduit. A hollow handle, which communicates between the vacuum source and the hollow conduit, defines a passageway for the aspirated debris.

The invention further relates to a suction device wherein the elongated section and part of the perforate end section are surrounded by a coaxially disposed perforate sleeve extending substantially from the end of the elongated section to the widest part of the perforate end section and having substantially the same size as the widest part of the end.

BRIEF DESCRIPTION OF THE DRAWINGS

FIG. 1 illustrates a preferred embodiment of a suction device used in the present invention.

FIG. 2 is an end view of the suction device shown in FIG. 1.

FIG. 3 illustrates the assembly of the device together with a hollow handle according to the invention.

FIG. 4 shows a preferred embodiment of the perforate sleeve intended to surround the elongated section and part of the perforate end section according to the invention.

FIG. 5 is an exploded perspective view of the assembly containing the device, sleeve, and handle, of the present invention.

FIG. 6 illustrates a surgical suction device, including a sleeve, according to the invention.

Throughout these drawings, like numbers are utilized to identify like parts.

DETAILED DESCRIPTION OF THE INVENTION

Figure 7:
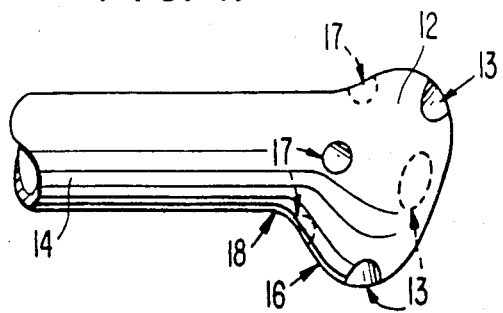
FIG. 7 illustrates an alternative embodiment of a suction device.

It has been discovered that a surgical suction device can be made convenient to use, clog resistant, efficient, and able to quickly clear an operating field of surgical debris while minimizing damage to tissue by disposing suction ports on a first surface portion of a perforate end section of the device so that these suction ports act as a vacuum modulator when suction ports on the second surface portion of the tip become clogged. Thus, debris which becomes lodged in suction ports on the second surface portion is not subjected to the entire vacuum because other ports remain open. Similarly, tissue is not traumatized by being strongly aspirated into the suction ports.

Lodged debris can often be dislodged simply by moving the device or rotating it within the operating field. Similarly, if the surgeon desires to remove a large particle from the field, the device simply can be removed from the field and wiped on another surface. The particle is easily removed from the suction ports because the vacuum is modulated by the non-plugged suction ports. Thus, the strength of the vacuum is automatically regulated without the need for a separate vacuum adjustment technique, such as the ability to expose additional suction ports in the tip. Further, debris which does become lodged in a suction port can be removed without the need for a shearing or cutting device.

It has also been discovered that the fraction of the total suction port area which is on the first portion of the end affects the self-regulation of vacuum distribution.

It has been further discovered that to orient the suction port conduits from the first surface portion, so that they intersect the hollow central suction conduit at approximately equal distances from the distal end and are disposed generally toward the distal end of the perforate end section, is desirable because this orientation creates turbulence at that intersection. This turbulence tends to ensure that particles aspirated into the hollow central suction conduit do not lodge in the intersection of the hollow conduit and the suction port conduits.

FIG. 1 illustrates a preferred embodiment of device 10 comprising elongated section 11 containing hollow central suction conduit 14 and perforate end section 12 through which hollow central suction conduit 14 continues. As illustrated, perforate end section 12 is bulbous. However, the perforate end of the tip need not be bulbous. Perforate end section 12 can have any enclosed shape which provides a first surface portion 16 extending outwardly from the end 18 of elongated section 11. Hollow central section conduit 14 continues through perforate end section 12. First surface portion 16 can be of any shape which is narrow at one end and widest at the other. An example of another suitable first surface portion is a frusto-conical section. Those skilled in the art are familar with other suitable first surface.

First surface portion 16 need not be oriented on the axis of hollow central suction conduit 14. Instead, first surface portion 16 could be oriented at an acute angle from the axis of hollow central suction conduit 14. FIG. 7 is an illustration of a tip with such an orientation. Further, hollow central suction conduit 14 need not be straight. It may have any curve or compound curves desired.

FIG. 2 depicts an end view of perforate end section 12, clearly illustrating a planar face 15 and the relationship between suction ports 13 in the second surface portion of perforate end section 12 and suction port 20 in planar face 15 of the second surface portion. The embodiment illustrated therein has three suction ports 13, each of which is substantially the same size, symmetrically placed about second surface portion of the perforate end section 12, and one suction port 20 centered in planar face 15. For the purpose of this invention, the suction ports 13 in the second surface portion of perforate end section 12 should be of the same size and these suction ports, together with suction port 20 in planar face 15, if the second surface portion has a planar face, should be symmetrically placed about the face and the second surface portion of the end, thus ensuring even distribution of suction.

Although the size of the suction ports is not critical, certain criteria should be considered when sizing the suction ports. As already described, the suction ports on the second surface portion of the end should be of the same size and symmetrically placed to ensure even distribution of the vacuum. Within these constraints, the number of suction ports is theoretically unlimited. However, practical considerations establish limits on the suction port size and placement. Although two suction ports could be symmetrically arranged on the second surface portion of perforate end section 12, the operability of the device would be reduced. Therefore, the fewest preferred number of suction ports in the second surface portion of the perforate end section 12 is three.

The suction ports communicate with hollow central suction conduit 14 via suction port conduits. Each suction port conduit preferably has the same cross-sectional size and shape as the suction port with which it communicates. However, the suction port conduit can have any cross-sectional size and shape which is not smaller than the cross-sectional size and shape of the associated suction port. This limitation ensures that solid or semi-solid particles of debris aspirated through the suction port will thus also be aspirated through the suction port conduit.

Figure 8:
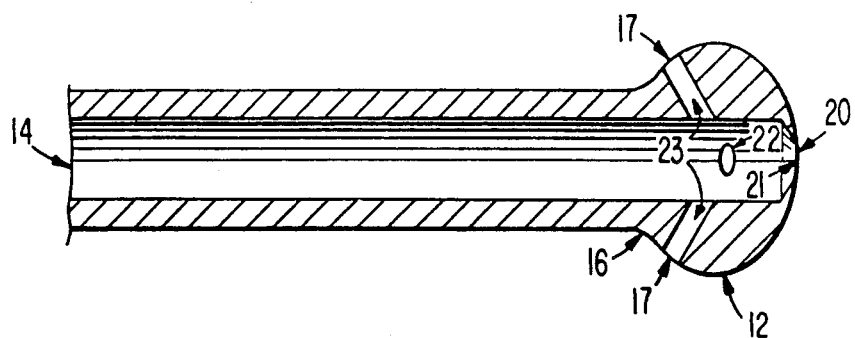
FIGS. 8 and 9 illustrate the relationship of the intersection of suction port conduits with the hollow central suction conduit.

Suction port conduits need not be any particular length. FIG. 8 illustrates the relative length of suction port conduits 23, in communication with suction ports 17 in first surface portion 16, and suction port conduit 21, in communication with suction port 20, in a preferred embodiment of this invention. Although suction port conduit 21 preferably is short, as illustrated in FIG. 8, it could be extended further into the interior of perforated end section 12.

The maximum number of suction ports is limited by the ability to manufacture a device having sufficient structural strength and by the minimum desired suction port size. The latter criterion establishes the practical limitation for the purposes of this invention, as the suction ports must be large enough to aspirate at least some of the non-fluid debris. This debris, such as fat globules, excised tissue, clotted blood, bone chips, and the like, can be removed either by aspirating the debris or by allowing the debris to become trapped in a suction port and then removing the suction device from the field to physically remove the entrapped debris. Therefore, those skilled in the art will be able to select the size for the suction ports disposed about the perforate end portion of the device and a symmetrical arrangement of these suction ports suitable for the purpose intended.

The suction device of this invention is particularly useful in orthopedic surgery. During such surgery, suction devices are required to remove dense viscous fluids, irrigating fluid, particles of bone and plastic, and similar debris. In such use, the preferred diameter of each of the three suction ports 13 in the second surface portion of the perforate end section 12 is between about 0.09 to 0.15 inch, more preferably between about 0.10 to 0.13 inch. Further, the preferred diameter of suction port 20 in planar face 15 is between about 0.15 to 0.20 inch, more preferably between about 0.16 to 0.18 inch. Such dimensions are advantageously utilized to aspirate the above-described debris. However, these guidelines should in no way be considered limiting because, as is clear to those in the art, other dimensions could be utilized advantageously in other applications.

FIG. 1 further illustrates placement of suction ports 17 in first surface portion 16 of perforate end section 12. The suction ports are preferably symmetrically arranged on first surface portion 16 and preferably are of equal size to ensure symmetrical distribution of the vacuum force. Because suction ports 17 on first surface portion 16 are not located on the same surface as are suction ports 13 and 20, they typically remain useful even if suction ports 13 and 20 become blocked for any reason. Thus, the device 10 can be advantageously utilized to aspirate pools of fluids containing solid and semi-solid debris which tends to block suction ports 13 and 20.

Suction ports 17 also function as an automatic vacuum modulator, facilitating operation of the tip under conditions conducive to blockage. Debris which becomes lodged in suction ports 13 and 20 is not subjected to the entire vacuum force because suction ports 17 remain open. Therefore, a large particle can be removed from the suction port with a simple wipe on a surgical towel, sponge, or other suitable area. The vacuum need not be temporarily interrupted to remove the blockage. Further, suction ports 17 continue to function while suction ports 13 and 20 are blocked, thus continuing to remove fluid and debris from the field.

The vacuum modulation feature of the tip of this invention also reduces trauma to aspirated tissue. Tissue aspirated into suction ports 13 and 20 does not typically receive the entire force of the vacuum because suction ports 17 will typically remain open. Therefore, injury to aspirated tissue is reduced.

When the device of this invention is used in orthopedic surgery, a preferred embodiment is to utilize three suction ports 17, each having a diameter of between about 0.06 to 0.11 inch, preferably between about 0.08 to 0.10 inch. The dimensions are advantageously used to aspirate debris from orthopedic surgery, but in no way should they be considered limiting. Those skilled in the art will be able to adapt the structure for use in surgery and applications wherein different suction port dimensions and arrangements will be effective.

Vacuum modulation is affected by the ratio of the cross-sectional area of the suction ports 13 and 20 on the second surface portion of perforate end section 12 to the cross-sectional area of the suction ports 17 on first surface portion 16. Therefore, those skilled in the art will be able to adjust this ratio to satisfy particular needs. For orthopedic surgery, a ratio between about 1.3 to 10 is suitable, with a ratio between about 1.9 to 4.3 preferable.

The suitability of this suction device is enhanced by its superior ability to aspirate bone chips and other solid or semi-solid debris such as fat globules, blood clots, excised tissue particles, and the like. If such material becomes lodged in a suction port, it can be removed by removing the device from the surgical field and wiping the tip. However, this invention is especially suitable for removal of semi-solids without disrupting the surgical procedure. First, it is sometimes possible to remove semi-solid blocking material merely by moving the device within the field to cause the semi-solid material to contact a plurality of suction ports. The additional force which will then be brought to bear on this semi-solid material is often sufficient to break the blockage into a plurality of pieces small enough to be aspirated. Second, it has been discovered that the suction port conduits can be arranged within the perforate end section to create turbulence at the intersections of the suction port conduits and the hollow central suction conduit within the device. This turbulence impinges upon that fraction of the blockage which is within the suction port conduit or which is caught on the intersection of the suction port conduits and hollow central suction conduit, and typically dislodges the blockage.

Figure 9:
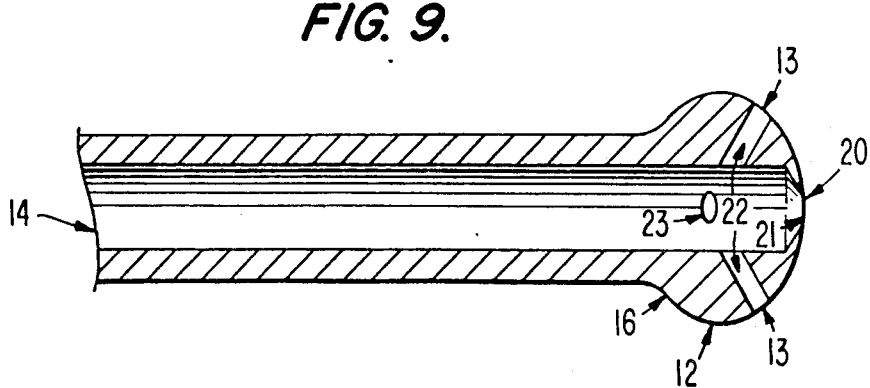

FIG. 8 illustrates the preferred orientation of suction port conduits 11, which are associated with suction ports 17 in first surface portion 16. The relative location of the intersection of one suction port conduit 22 with hollow central suction conduit 14 is also illustrated. Similarly, FIG. 9 illustrates the preferred orieintation of suction port conduits 22, which are associated with suction ports 13 in the section surface portion of perforate end portion 12. The relative location of the intersection of one suction conduit 23 with hollow central suction conduit 14 is also shown. Each figure also illustrates the location of suction port 20 and suction port conduit 21.

Although suction port conduits 23 and 22 could be disposed perpendicular to hollow central suction conduit 14, the preferred arrangements are illustrated in FIGS. 8 and 9. Preferably, hollow central suction conduit 14 and suction port conduits 23 intersect at approximately equal distances from the distal end of perforate end section 12, and suction port conduits 23 are disposed generally in the direction of the distal end of perforate end section 12. Further, suction port conduits 22 preferably intersect hollow central suction conduit 14 at approximately equal distance from the distal end of perforate end section 12, and suction port conduits 22 are disposed generally away from the distal end of perforate end section 12. Finally, the intersections of hollow central suction conduit 14 with suction port conduits 22 are preferably closer to the distal end of perforate end portion 12 than are the intersections of hollow central suction conduit 14 with suction port conduits 23.

FIG. 8 further illustrates that hollow central suction conduit 14 preferably has a diameter larger than any of the suction ports and suction port conduits so that aspirated material does not become lodged within the device. To dislodge such a blockage would require taking the device out of service and manually removing the blockage. In a preferred embodiment for orthopedic surgery, hollow central suction conduit 14 has an interior diameter of approximately 0.18 to 0.23 inches, and is preferably larger than the largest suction port or suction port conduit. Those skilled in the art can change this diameter to one more suitable for their intended use.

FIG. 3 illustrates the use of the device in conjunction with hollow handle 30. As can be seen in the figure, handle 30 is hollow so as to form a passageway for aspirated debris from hollow central suction conduit 14 to the vacuum source and is adapted at one end 31 to be removably connected to hollow central suction conduit 14, and at the other end 32 to be attached to a vacuum source. The particular method of removably attaching these parts to each other is not critical to the invention. Although a typical friction-type hose connection is illustrated at end 32 where hollow handle 30 is attached to the vacuum source, any vacuum-tight connection technique known to those skilled in the art could be utilized. Similarly, illustrated threaded connection 31 could be a slip-joint (lug and slot), a snap-joint, or any other vacuum-tight connection technique. A positive retention technique is preferred so that the device does not become dislodged or disconnected from the handle during surgery. A threaded joint is preferred.

The inside diameter of hollow handle 30 should be no less than the inside diameter of hollow central suction conduit 14. Further, although no special design need be placed on the surface of handle 30, if desired, an anti-slip surface such as the diamond pattern illustrated in part in FIG. 6 can be employed. Further, suitable coating material can be utilized. The outside diameter of the hollow handle 40 is preferably the same as that of the sleeve and is adapted to abut sleeve 40.

Device 10 is also adapted to receive perforated sleeve 40, illustrated in FIG. 4. The particular method of attachment of sleeve 40 to device 10 is not critical for this invention. FIG. 5 illustrates the relationship between a substantial portion 40' of sleeve 40 and device 10, and FIG. 6 depicts an entire assembly including device 10 (of which only the second surface portion of perforate end section 12 is visible), sleeve 40, and handle 30. Although no positive attachment device need be utilized, such a device is preferred. Great strain is placed on the sleeve when, for example, the device is utilized to suction a long bone in orthopedic surgery.

One skilled in the art could select a suitable method for positively securing sleeve 40 to device 10. For example, shoulder 19 or perforated end section 12 could be threaded and the appropriate end of sleeve 40 oppositely threaded. Similarly, a retaining pin or lug could be placed on shoulder 19 or perforated end section 12 and a slot appropriately placed on sleeve 40 and shaped so that the pin is received in the slot to retain sleeve 40. If desired, the lug or pin portion of the retention device could be attached to the exterior of elongated section 11. Of course, other positive retention devices can be utilized.

Preferably, the outside dimension of handle end 31 and the widest dimension of perforate end section 12 are substantially equal, and the largest dimension of shoulder 19 is slightly smaller than the handle. Then, the inside dimension of sleeve 40 can advantageously be selected so that sleeve 40 can be put in place by removing device 10 from handle 30, sliding sleeve 40 over shoulder 19 of device 10 so that one end abuts against the widest dimension of perforate end section 12, and, upon replacement of device 10 on handle 30, the other end of the sleeve abuts handle end 31. Further, the sleeve must not block suction ports 17. It is also preferred that the outside dimension of sleeve 40 equal to the widest dimension of perforate end section 12. Finally, the ends of the walls of sleeve 40 are preferably shaped to match the shape of those portions of handle end 31 and perforate end section 12 against which sleeve 40 abuts. Matching shapes in this fashion helps ensure not only that sleeve 40 is properly centered and retained on device 10, but also that vacuum is directed to sleeve 40 and not to the joint between sleeve 40 and perforate end section 12.

Alternatively, other types of retainers can be utilized. Sleeve 40 can be urged over the largest dimension of perforate end section 12 and held against knob or shoulder 19 of device. Appropriate selection of the dimensions of sleeve 40, shoulder 19, and perforate end section 12 allows sleeve 40 to be retained on device 10 by force or friction. However, this embodiment is not preferred when stress placed on the sleeve might cause the sleeve to be dislodged.

Perforations in sleeve 40 should be smaller than suction ports 17 to avoid blocking suction ports 17 while the sleeve is in place. Any solid which is aspirated through the sleeve perforations will thus also be aspirated through the larger suction ports 17. Further, the distance between the interior of sleeve 40 and the exterior of elongated section 11 should be least as large as the perforations in sleeve 40 so that aspirated material does not lodge between the sleeve and the elongated section. The diameter and arrangement of the perforations can be selected by one skilled in the art.

Sleeve 40 is intended for use in situations where the volume of liquids to be aspirated is large, or when the device must be inserted into a deep field. Therefore, use of sleeve 40 is preferred during orthopedic surgery, because large volumes of irrigating fluid are typically used to clear the operating field of blood, bone chips, and the like. Further, the device must often be inserted deep into or along side of a bone such as the femur. For such use, the perforations in the sleeve preferably have a diameter between about 0.05 to 0.10 inch, preferably between about 0.07 to 0.09 inch, but preferably smaller than that of suction ports 17. When perforate end section 12 is not placed symmetrically about the longitudinal axis of hollow central section conduit 14, the design of the sleeve must be adjusted to accommodate the asymmetry, if possible.

Sleeve 40 is also useful in reducing trauma to tissue. In situations where it is necessary to insert device 10 deep into an area surrounded by tissue, or deep into a long bone, as in orthopedic surgery, sleeve 40 can be advantageously by used to ensure that tissue or solid and semi-solid debris do not block suction ports 17.

The superior performance of the device of this invention can be utilized advantageously by reducing the size of the device. For example, the widest dimension of the preferred bulbous perforate end section 12 for use in orthopedic surgery as described above, is between about 0.30 to 0.50 inch, preferably between about 0.32 to 0.44 inch. The length of elongated section 11 can be selected to meet the user's needs. For orthopedic surgery, lengths of between about 2 to 3 inches are preferred.

Any of the appropriate materials of construction for surgical devices can be utilized to manufacture the device of this invention. The material must be sterilizable and able to withstand the rigors of a surgical field and the force of the vacuum. Preferably, the entire assembly is lightweight to mitigate fatigue. If desired, it can be made disposable. Further, care should be taken to ensure that there are no sharp edges on this device, especially at the distal end of the sleeve.

The following example describes an embodiment of the device of this invention.

EXAMPLE

A device having a bulbous end as illustrated in FIG. 1 was fashioned from stainless steel. The widest dimension of the bulb was 0.37 inches and the length of the elongated section was 2⅛ inches. The interior diameter of the hollow central suction conduit was 0.20 inches and the hollow handle had an inside diameter of 0.23 inches and an outside diameter of 0.38 inches. The suction ports and suction port conduits were circular and were sized as follows:

| Suction Port Identity | Quantity | Diameter, inc |
| --- | --- | --- |
| Planar face of distal end (20) | 1 | 0.17 |
| Second surface portion of end (13) | 3 | 0.11 |
| First surface portion of end (17) | 3 | 0.09 |

Each set of suction ports was disposed symmetrically on a circle, i.e., equidistant from the distal end of the device. Suction port 20 was located in the center of planar face 15 of the second surface portion. The remaining ports were symmetrically disposed on circles at 120° intervals. The intersections of suction port conduits 22 with hollow central suction conduit 14, were equidistant from, albeit closer to, the distal end of perforate end portion 12 then were the intersections of suction port conduits 11 with hollow central suction conduit 14.

This device was utilized in orthopedic surgery to remove bone chips and completely dry the operating field. The surgery proceeded quickly, and the amount of tissue trauma was reduced.

Although preferred embodiments of this invention have been disclosed herein, those skilled in the art will appreciate that changes and modifications may be made without departing from the spirit of this invention, as defined in and limited only be the scope of the appended claims.

I claim:

1. A suction device for attachment to a vacuum source for removal of surgical debris comprising: an elongated section containing a hollow central suction conduit and having a first end opposite a perforate end section extending outwardly from said elongated section and through which said central suction conduit continues, the perforations in the surface of said perforate end section forming suction port openings which communicate with said central suction conduit via suction port conduits through said perforate end section; said perforate end section having a first surface portion with at least one suction port opening thereon extending from the end of said elongated section to the widest part of said end section, which is wider than said elongated section, and a second surface portion with at least one suction port opening thereon extending from the widest part of said end section to the distal end of said end section; and a perforated sleeve disposed coaxially with the elongated section extending from the widest part of the perforate end section to the first end of the elongated section.

2. The suction device of claim 1 additionally comprising a handle portion removably connected to the first end of said elongated section containing a passageway in communication with said central suction conduit and a source of vacuum, and through which the debris can be aspirated.

3. The suction device of claim 1 wherein the ratio of the surface area of the suction port openings in the second portion to the surface area of the suction port openings in the first portion is between about 1.3 to 10.

4. The suction device of claim 3 wherein the ratio of the surface area of the suction port openings in the second portion to the area of the suction port openings in the first portion is between about 1.9 to 4.3.

5. The suction device of claim 1 wherein said suction port openings are arranged symmetrically about said perforate end section.

6. The suction device of claim 1 wherein the second surface portion of said perforate end section terminates in a planar face portion at the distal end of said end section.

7. The suction device of claim 6 wherein said face portion has one circular suction port opening of a diameter of from about 0.15 to 0.20 inches, wherein the remainder of said second surface portion has symmetrically disposed therein three circular suction port openings each having a diameter of from about 0.09 to 0.15 inches, and wherein said first surface portion has symmetrically disposed therein three circular suction ports each having a diameter of from about 0.06 to 0.11 inches.

8. The suction device of claim 7 wherein said suction port opening in said face portion has a diameter of between about 0.16 to 0.18 inches, said suction port openings in the remainder of said second surface portion having diameters between about 0.10 to 0.13 inches, and said suction port openings in said first surface portion have diameters between about 0.08 to 0.10 inches.

9. The suction device of claim 1 wherein the perforations of said perforate sleeve are smaller than said suction ports in said first surface portion.

10. The suction device of claim 1 wherein the suction port conduits from said first surface portion intersect said central suction conduit at points approximately equidistant from the distal end of said perforate end section, and said section part conduits are disposed so that the suction port openings are further from the distal end of said perforate end section than are the intersections of said suction port conduits with said central suction conduit.

11. The suction device of claim 10 wherein the suction port conduits from said second surface portion intersect said central suction conduit at points approximately equidistant from the distal end of said perforate end section, and said suction port conduits are disposed so that the suction port openings are closer to the distal end of said perforate end section than are the intersections of said suction port conduits with said central suction conduit.

* * * * *